(12) United States Patent
Solis Herrera

(10) Patent No.: US 10,722,728 B2
(45) Date of Patent: Jul. 28, 2020

(54) TEXTILE COVERED WITH AN ACTIVE OUTSIDE SURFACE AND AN ACTIVE INSIDE SURFACE COMPRISING OPTICAL FIBERS

(71) Applicant: Arturo Solis Herrera, Aguascalientes (MX)

(72) Inventor: Arturo Solis Herrera, Aguascalientes (MX)

( * ) Notice: Subject to any disclaimer, the term of this patent is extended or adjusted under 35 U.S.C. 154(b) by 75 days.

(21) Appl. No.: 15/553,281

(22) PCT Filed: Feb. 5, 2016

(86) PCT No.: PCT/IB2016/050596
§ 371 (c)(1),
(2) Date: Aug. 24, 2017

(87) PCT Pub. No.: WO2016/135573
PCT Pub. Date: Sep. 1, 2016

(65) Prior Publication Data
US 2018/0043179 A1    Feb. 15, 2018

(30) Foreign Application Priority Data

Feb. 24, 2015 (LU) .......................................... 92661

(51) Int. Cl.
*A61N 5/06* (2006.01)
*D03D 1/00* (2006.01)

(52) U.S. Cl.
CPC ......... *A61N 5/0618* (2013.01); *D03D 1/0088* (2013.01); *A61N 2005/063* (2013.01); *A61N 2005/0645* (2013.01); *A61N 2005/0657* (2013.01); *A61N 2005/0662* (2013.01); *D10B 2401/20* (2013.01)

(58) Field of Classification Search
CPC .......... A61N 5/0618; A61N 2005/0657; A61N 2005/0645; A61N 2005/063; A61N 2005/0662; D03D 1/0088; D10B 2401/20
See application file for complete search history.

(56) References Cited

U.S. PATENT DOCUMENTS

| 6,034,003 | A  | * | 3/2000 | Lee ..................... D06M 13/123 |
|           |    |   |        | 442/130                            |
| 6,290,713 | B1 | * | 9/2001 | Russell ................ A61N 5/0616 |
|           |    |   |        | 607/88                             |

(Continued)

FOREIGN PATENT DOCUMENTS

| CN | 101718020     | 6/2010 |
| CN | 202314978     | 7/2012 |
| EP | 2 422 844 A1  | 2/2012 |

OTHER PUBLICATIONS

Search Report dated Oct. 9, 2015, of corresponding LU Application No. 92661, along with the Written Opinion in English.

(Continued)

*Primary Examiner* — Catherine M Voorhees
(74) *Attorney, Agent, or Firm* — DLA Piper LLP (US)

(57) ABSTRACT

A textile has an active outside surface and an active inside surface including optical fibers covering at least partially the active outside surface, wherein the active outside surface captures light, which is transmitted by the optical fibers to the active inside surface.

16 Claims, 3 Drawing Sheets

(56) References Cited

U.S. PATENT DOCUMENTS

| | | | | |
|---|---|---|---|---|
| 7,234,853 B2* | 6/2007 | Givoletti | ............... | B60R 13/02 160/10 |
| 8,783,903 B2* | 7/2014 | Bhattacharya | ............ | G09F 9/33 29/592.1 |
| 2013/0281913 A1* | 10/2013 | Piergallini | ............. | A61K 41/00 604/20 |
| 2014/0052050 A1* | 2/2014 | Courtin | ............... | A61N 5/0616 604/20 |
| 2014/0277294 A1* | 9/2014 | Jones | .................... | A61N 5/062 607/88 |
| 2016/0129279 A1* | 5/2016 | Ferolito | .............. | A61N 5/0618 607/89 |
| 2016/0220840 A1* | 8/2016 | Mordon | ................ | A61N 5/062 |

OTHER PUBLICATIONS

Notification of Transmittal of the International Search Report and the Written Opinion of the International Searching Authority dated May 12, 2016 of corresponding International Application No. PCT/IB2016/050596.

International Preliminary Report on Patentability dated Sep. 8, 2017, of corresponding International Application No. PCT/IB2016/050596.

Office action dated Dec. 26, 2016, of corresponding Taiwanese Application No. 105104864, along with an English translation.

Office Action dated Oct. 16, 2019, of counterpart Russian Application No. 201791594/31, along with a Summary of Office Action in English.

Office Action dated Oct. 31, 2019, of counterpart European Application No. 16709583.5, along with a Summary of Office Action.

* cited by examiner

TEXTILE COVERED WITH AN ACTIVE OUTSIDE SURFACE AND AN ACTIVE INSIDE SURFACE COMPRISING OPTICAL FIBERS

TECHNICAL FIELD

This disclosure relates to an alternative to a medical therapy of avoiding seasonal affective disorder (SAD), particularly by providing light to human skin at all times even though the human is covered with a textile.

BACKGROUND

Seasonal affective disorder, also known as winter depression, winter blues, summer depression, summer blues, or seasonal depression, was considered as a mood disorder in which people who have normal mental health throughout most of the year experience depressive symptoms in the winter.

Winter depression is a common slump in the mood of some inhabitants of most of the Nordic countries.

In the Diagnostic and Statistical Manual of Mental Disorders, winter depression is no longer classified as a unique mood disorder, but is now a specifier called with seasonal pattern for recurrent major depressive disorder that occurs at a specific time of the year and fully remits otherwise. Although experts were initially skeptical, this condition is now recognized as a common disorder. SAD's prevalence in the U.S. ranges from 1.4% in Florida to 9.9% in Alaska.

The U.S. National Library of Medicine notes that some people experience a serious mood change when the seasons change. They may sleep too much, have little energy, and may also feel depressed. Though symptoms can be severe, they usually clear up.

There are many different treatments for classic (winter-based) seasonal affective disorder.

Treatments for classic (winter-based) seasonal affective disorder include light therapy, medication, ionized-air administration, cognitive-behavioral therapy and carefully timed supplementation of the hormone melatonin.

Photoperiod-related alterations of the duration of melatonin secretion may affect the seasonal mood cycles of SAD. This suggests that light therapy may be an effective treatment for SAD. Light therapy uses a lightbox emitting far more lumens than a customary incandescent lamp. Bright white "full spectrum" light at 10,000 lux, blue light at a wavelength of 480 nm at 2,500 lux or green light at a wavelength of 500 nm at 350 lux are used, with the first-mentioned historically preferred.

Bright light therapy is effective with the patient sitting a prescribed distance, commonly 30-60 cm, in front of the box with her/his eyes open, but not staring at the light source for 30-60 minutes. But many of patients find lightbox treatment inconvenient and as many stop use because of this.

Dawn simulation has also proven to be effective in some studies.

Light therapy can also consist of exposure to sunlight, either by spending more time outside or using a computer-controlled heliostat to reflect sunlight into the windows of a home or office. Although light therapy is the leading treatment for seasonal affective disorder, prolonged direct sunlight or artificial lights that don't block the ultraviolet range should be avoided due to the threat of skin cancer.

SSRI (selective serotonin reuptake inhibitor) antidepressants have proven effective in treating SAD, also. Bupropion is also effective as a prophylactic. Effective antidepressants are fluoxetine, sertraline, or paroxetine.

An explanation for winter depression is that vitamin D levels are too low when people do not get enough Ultraviolet-B on their skin. Thus, an alternative to using bright lights is to take vitamin D supplements.

Another disorder of a reduced light exposure is the change of the human skin during the winter period, whereupon the skin dries out and remoisturization of the skin is disturbed due to the reduced light exposure. That results in the consequence often, that humans develop neurodermatitis in the winter.

The problems of the therapies known in the state of the art are beside the undesirable effects during and after the administration of hormones, antidepressants and vitamin D to the humans that many of patients find lightbox treatment inconvenient and as many stop use because of this. Moreover the exposure to sunlight or artificial light needs time and requires the patient removes most of their clothes.

It could therefore be helpful to find a human exposure to light in all situations when light from a light source is available, particularly, to find a possibility that human skin can be exposed to light even though the human is covered with clothes.

SUMMARY

I provide a textile having an active outside surface and an active inside surface including optical fibers covering at least partially the active outside surface, wherein the active outside surface captures light, which is transmitted by the optical fibers to the active inside surface.

I also provide a garment for a human including at least the textile having an active outside surface and an active inside surface including optical fibers covering at least partially the active outside surface, wherein the active outside surface captures light, which is transmitted by the optical fibers to the active inside surface.

I further provide a method of producing a garment including forming the textile having an active outside surface and an active inside surface including optical fibers covering at least partially the active outside surface, wherein the active outside surface captures light, which is transmitted by the optical fibers to the active inside surface into a shape suitable to fit over and be worn by a human.

Figure 1:
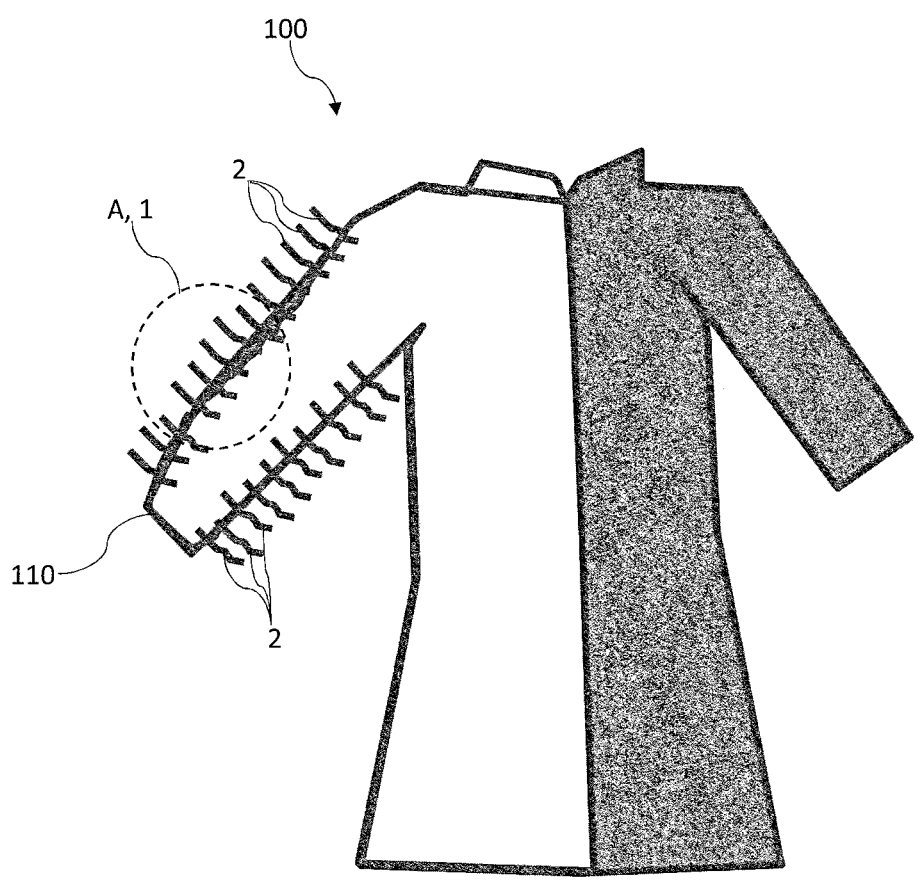
FIG. 1 is a schematic drawing of a garment made at least of my textile.

REFERENCE NUMERAL LIST 1 textile
2 optical fiber/textile-processable fiber
3 active/optical outside surface
4 active/optical inside surface
5 material layer of the textile 1
6 end of the optical fiber on the active/optical outside surface
7 end of the optical fiber on the active/optical inside surface
A detailed view of a textile

DETAILED DESCRIPTION

The active outside surface of the textile captures light with optical fibers, which is transmitted by the optical fibers to the active inside surface of the textile. The active inside or inner surface of the textile is closed to the skin or is in contact to the skin so that light transmitted by the optical fibers from the outside surface to the inner surface of the textile strikes the skin of a human, who is covered with the textile. Therefore, there is no longer a need to remove clothes made of my textile to expose human skin with light, so that symptoms occurring from deficiency supplying light to human are reduced, especially in the winter time. With the active outer surface light from a light source is captured and transmitted directly to the active inside or inner surface of such an article of clothing made of my textile. Thus, the human wearing such an article of clothing is exposed to light in all situations when a light source is available. So every step a human makes outside a building or near a light source emitting natural light such an article of clothing helps to reduce the risk of depression or other diseases such as neurodermatitis in connection with the decreased light exposure, especially in the winter period.

As mentioned above, the light is captured by optical fibers on the active outside surface of the textile. Thus, preferably, the active outside surface and the active inside surface comprise the optical fibers. Also, preferably, the active outside surface and the active inside surface are formed by the optical fibers, whereupon the entire active outside surface and/or the active inside surface is covered with the optical fibers. To transmit light through the optical fibers from the outside surface to the inside surface, the optical fibers work as a light conductor system to bring the light captured by the outside surface over the optical fibers, which function as a wire for the light, to the inside surface of the textile by which the light is dissipated to the human skin, which notably means that the active outside surface and the active inside surface are connected by the optical fibers, preferably.

Advantageously, the textile is used for the production of a garment. Moreover, the textile can be used as any other material, for example, as bed linen or as a roof of a tent, as a marquee or an awning. Preferably, the textile or the optical fibers forming the textile can also be used as building material. If a wall of a building is made of such a material, the outer surface of the wall forms the active outside surface and the inner surface of the wall forms the active inside surface. Therefore, the wall, for example, a house wall, functions as a light conductor system, whereby light is captured by the outer surface and transmitted by the optical fibers to the inner surface of the wall, whereby the inner surface dissipates the light into the house.

Preferably, the optical fibers are textile-processable fibers, which can be used to manufacture the textile. Beside the optical transmittance, the fibers closely resemble wool in its character, advantageously. Furthermore, the fibers or the textile made of such fibers should be easy to wash and should have good dimensional stability, resistance to damage by moths and chemical substances, excellent color-fastness and dyeability in brilliant colors, highly resistant to sunlight. Other beneficial properties of the fibers or the textile made of such fibers are lightweight, soft, and warm, with a wool-like touch. Therefore, the textile also fulfills thermo-insulating function.

Advantageously, the textile-processable fibers, that are the optical fibers, are made of transparent plastic sometimes called acrylic glass or extruded glass (silicia), which are slightly thicker than a human hair in an especially advantageous manner and which can function as a waveguide, or "light pipe", to transmit light between the two ends of the fiber. Thereby, the fibers are made of Polymethylmethacrylate (PMMA), Polycarbonate (PC) modified formulations with varying amounts of other comonomers, additives, and fillers are created for uses where specific properties are required as, for example, a small amount of acrylate comonomers used in PMMA or in PC, whereupon the small amount of acrylate comonomers grades destined for heat processing, since this stabilizes the polymer to depolymerization ("unzipping") during processing. Other comonomers such as butyl acrylate can be added to improve impact strength. Moreover, comonomers such as methacrylic acid can be added to increase the glass transition temperature of the polymer for higher temperature use such as in lighting applications. Plasticizers may be also added to improve processing properties, lower the glass transition temperature, or improve impact properties. Preferably, dyes can be added to give color for decorative applications, or protect against (or filter) UV light. To improve cost-effectiveness, fillers may be added to the material from which the fibers are made.

Advantageously, the textile-processable or optical fibers are treated superficially, in particular the textile-processable or optical fibers are damaged in a defined manner so that light is captured at the end and/or the lateral of the fibers and the light is dissipated over the lateral surface and/or over the opposite end of the fibers. Furthermore, the optical fibers can include a transparent core surrounded by a transparent cladding material with a lower index of refraction. This has the advantage that light is kept in the core by total internal reflection. This causes the fiber to act as a waveguide. Thus, preferably, the fibers can be Hard-clad silica (HCS) or polymer-clad fibers (PCF) with a core of silica glass (diameter: 200 µm) and an optical cladding made of special plastic (diameter: 230 µm).

The optical or textile-processable fibers are preferably knitted, woven, tufted or sewn in the textile to build an active outer surface and an active inner surface. Therefore, already existing textile, garment or clothing made of a textile can be modified to capture light with an outer surface and transmit the light through the textile or clothing to an inner surface that dissipates the light to a human skin wearing such a textile, garment or clothing. Thus, the garment or clothing is outer clothing for men, women and children made of my textile.

To transmit light through the garment, clothing or textile as much as possible to the human skin the optical fibers should cover at least partially the outside surface, wherein the outside surface is connected by the optical fibers with an active inside surface. But covering the entire outside surface to control the light capture area is still the preferred choice to strike light captured by the outside surface to human skin as much as possible by dissipating the light by the inner active surface to the human skin, whereupon the light is transmitted by the optical fibers from the outer surface to the inner surface.

Because the outer surface is connected via the optical fibers to the inner surface of the garment or clothing, the garment or clothing can be used in a very favorable way to illuminate outer clothing with a light source transmitting light from the active inner surface to the active outer surface via the optical fibers. The light source could be an LED or another electrical light source which is electrically powered by an electrical power supply, for example, a battery or an accumulator.

I also provide a method of manufacturing a textile capable of capturing light, preferably my textile to produce a garment or a clothing, wherein the garment or the clothing is capable of giving the captured light to the human skin.

To avoid any repetition regarding the potential benefits of the method, one is referred to the description of my textile and one is referred completely to this description.

The textile can be made of a material comprising melanin and/or derivative, analogues, or precursors of melanin. Therefore, preferably, the material used for the textile is mixed with melanin and/or derivative, analogues, or precursors of melanin, advantageously, that melanin and/or the derivative, analogues, or precursors of melanin is an additive of the material used for my textile.

It is possible for the manufacturing of the textile, that the material is, stained, coated and/or impregnated with melanin and/or the derivative, analogues, or precursors of melanin, whereupon, preferably, the material is formed as a fabric, including leather and/or fibers.

A garment or clothing made of a textile comprising melanin and/or derivative, analogues, or precursors of melanin has the advantage that melanin is able to absorb any kind of energy, for example, kinetic energy, electromagnetic radiation, elastic energy or electric energy and then dissipates the energy in a non-radiative way, in which the capacity of melanin and/or derivative, analogues, or precursors of melanin is the result of the ability to split and reform water molecule. This capacity of melanin and/or derivative, analogues, or precursors of melanin is used for the textile, preferably for the garment or clothing made of such a textile, whereupon the garment or clothing is comfortable to wear all year, independent from cold or hot temperatures. In hot months, melanin and/or derivative, analogues, or precursors of melanin dissipate the excess of heat bringing the temperature of the closet area to the garment or to the clothing within a range of temperature that is friendly with the physiology of the human being. Therefore, textile comprising melanin and/or derivative, analogues, or precursors of melanin is able to increase the temperature preferably from 1° C. to 5° C., still preferred from 6° C. to 10° C. and most preferred more than 10° C. above room temperature. In contrast or in addition, the temperature of the textile comprising melanin and/or derivative, analogues, or precursors of melanin is able to reduce the temperature of a garment or a clothing preferably from 5° C. to 10° C., still preferred from 10° C. to 20° C. and most preferred more than 20° C. below the room temperature.

My textiles, fabrics, garments and methods are further described in detail with respect to the accompanying drawings. Features discussed within the description of the drawings can be combined each other freely and can be combined with the features discussed within the specification each other freely. The features mentioned in the claims, in the specification and in the description of the drawings are essential, either in themselves or in any given combination.

In the different figures, the same features always correspond to the same reference signs, therefore generally the features are only described once.

The example of a garment 100 depicted in FIG. 1 shows a jacket covered at least partially with the textile 1. In this case the left side of the garment 100, namely at least the jacket sleeve 110 is formed with the textile 1 comprising optical fibers 2. With the active outside surface 3 of the textile 1, the jacket captures light, which is transmitted via the optical fibers 2 to an active inside surface 4 of the textile 1. From the active inside or inner surface 4 the light is dissipated to the skin of a human wearing the jacket. In the example of the jacket as the garment 100 shown in FIG. 1, the left side is schematically illuminated, but the right side of the jacket not covered with optical fibers 2 is not illuminated. Therefore, if the entire garment 100 is covered with optical fibers 2, this means if the whole jacket is made of the textile 1, the garment 100 captures light over the entire outside surface of the garment 100, whereupon the light is transmitted via the optical fibers 2 to the whole inside surface of the garment 100 and from there to the human skin that is covered by the garment 100. Therefore, over the entire textile area of the garment 100 light is transmitted at all times a light source is available so that light the human body needs to function properly is dissipated to the human skin at all times a light source is available while the garment 100 is being worn. At the same time, such a garment 100 is given cold insulation because of the arrangement of the optical fibers 2 or of the fibers 2 themselves. Such an optical fiber arrangement is shown in the following figures.

Figure 2:
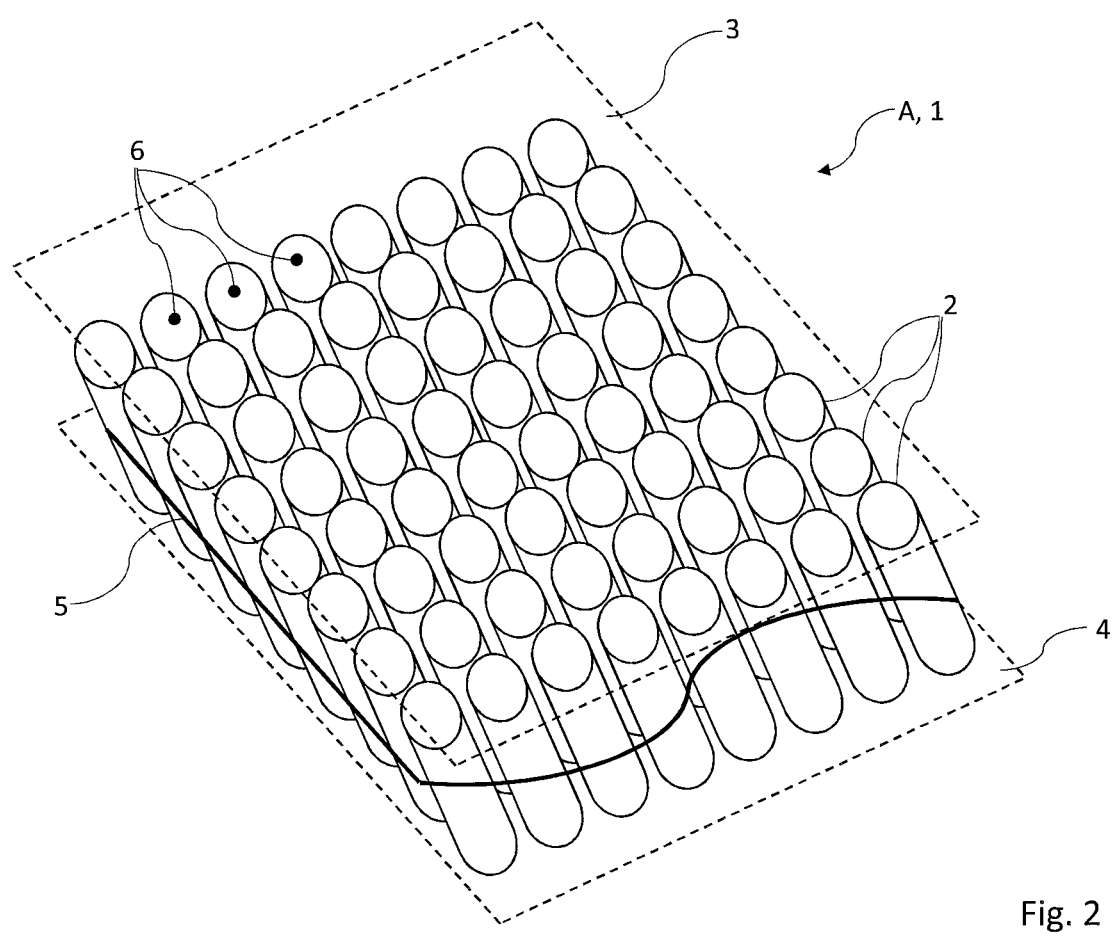
FIG. 2 is a detailed view on the section A marked with dotted line in FIG. 1 on a textile having an active outside surface and an active inside surface comprising optical fibers with a view to the active outside surface.
Figure 3:
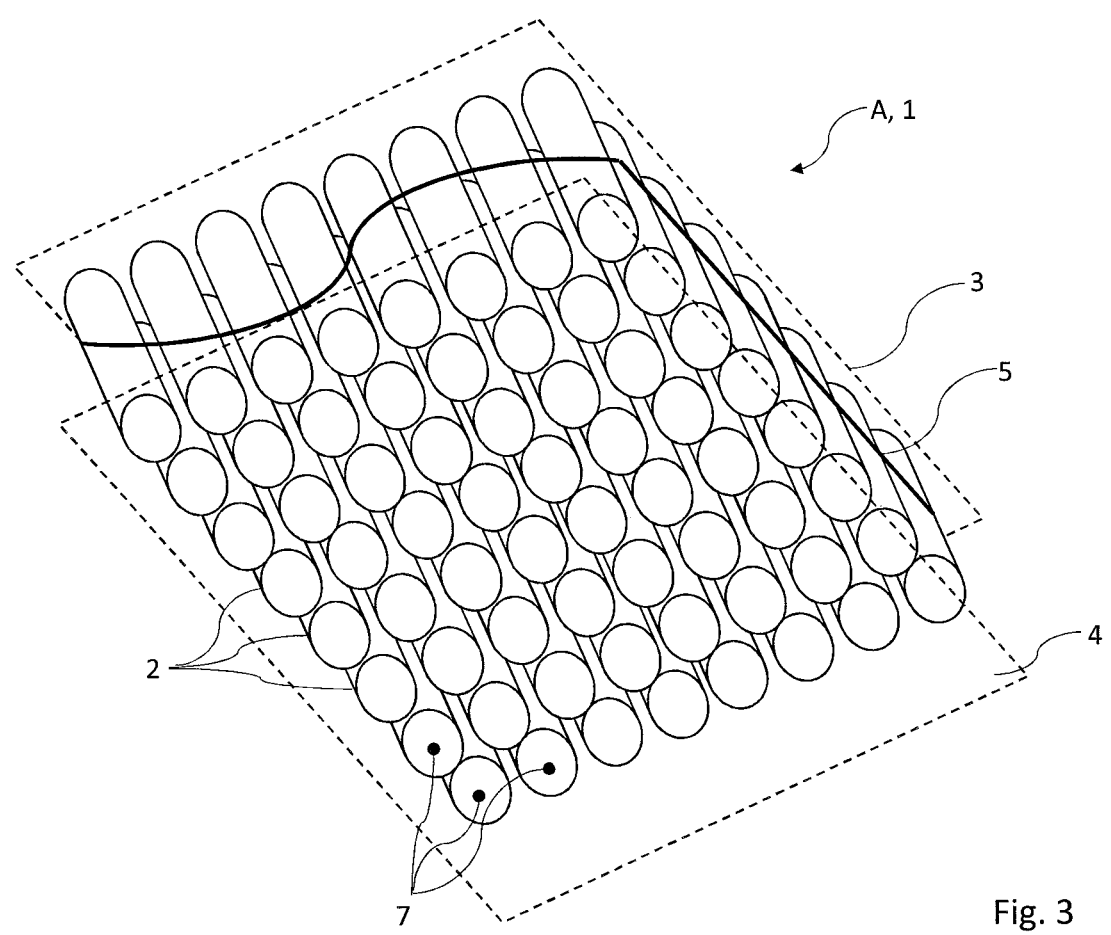
FIG. 3 is the detailed view of FIG. 2 with a view on the active inside surface.

FIGS. 2 and 3 show detailed views of the section A marked with dotted line in FIG. 1 on a textile 1 having an active outside surface 3 and an active inside surface 4 comprising optical fibers 2, with a view to the active outside surface 3 of the textile 1 in FIG. 1 and with a view to the active inside surface 4 that is close to the human skin or in contact with the human skin in FIG. 2. The active outside surface 3 and the active inside or inner surface 4 are indicated with dotted lines. The optical fibers 2 cover the entire active outside surface 3 of the textile 1 or form with the ends 6 of the optical fibers 2 the active outside surface 3 or form with the ends 7 of the optical fibers 2 the active inside surface 3. As shown, the active outside surface 3 is connected via the optical fibers 2 with the active inside surface 4, whereupon the optical fibers 2 are passed through a material layer 5 of the textile 1. Therefore, light is captured with the ends 6 of the optical fibers 2 on the active outside surface 3. From the active or optical outside surface 3, the light is passed through the material layer 5 of the textile 1 by transmitting it through the optical fibers 2 to the active or optical inside surface 4. From the ends 7 of the optical fibers 2 which are arranged on the active inside surface 4 or which form the active or optical inside surface 4, the light is dissipated to the skin of a human who is covered with the textile 1. In the example shown in the figures, the optical fibers 2 are in spatial arrangement covering the entire active outside surface 3 and the entire active inside surface 4 of the textile 1 so that the textile 1 has thermo-insulating effect, also. The spatial arrangement of the fibers 2 causes that air is kept between the optical fibers 2, whereby at least the air between the fibers 2 or the fibers 1 themselves have thermo-insulating effect. Contrary to the spatial-arrangement of the optical fibers 2 within the textile 1 and the nearly-vertical slope of the fibers 2 to the material layer 5 of the textile 1 as shown in the figures, the optical fibers 2 can be arranged also differently, as long as light can be captured on the active outside surface 3, preferably with the ends 6 of the optical fibers 2, and as long the light is transmitted via the optical fibers 2 to the active inside surface 4, preferably to the other ends 7 of the optical fibers 2, from where the light is dissipated to human skin, who is covered by the textile 1 comprising the optical fibers 2.

The invention claimed is:

1. A textile having an active outside surface and an active inside surface comprising optical fibers covering at least partially the active outside surface, wherein the active outside surface captures light, which is transmitted by the optical fibers to the active inside surface, wherein the textile is made of a material comprising melanin or derivatives of melanin, wherein the optical fibers are passed through a material layer of the textile, wherein light is captured with ends of the optical fibers on the active outside surface, whereupon the light is passed through the material layer of the textile by transmitting through the optical fibers to the active or optical inside surface, and wherein from opposing ends of the optical fibers which are arranged on the active inside surface or which form the active or optical inside surface the light is dissipated in a non-radiative way to the skin of a human who is covered with the textile and regulates a temperature of a microenvironment between the skin of the human and the textile.

2. The textile as claimed in claim 1, wherein at least the entire active outside or the entire active inside surface is covered with the optical fibers, said active outside surface and the active inside surface are connected by the optical fibers, and said active inside surface dissipates the light captured by the active outside surface.

3. The textile as claimed in claim 1, wherein the optical fibers are textile-processable fibers.

4. The textile as claimed in claim 1, wherein the optical fibers are made of Polymethylmethacrylate (PMMA), Polycarbonate (PC), or Polymethylmethacrylate (PMMA), Polycarbonate (PC) modified formulations with varying amounts of other comonomers, additives, and fillers or are made of extruded glass (silicia).

5. The textile as claimed in claim 3, wherein optical fibers are treated superficially so that the textile-processable fibers are damaged in a defined manner so that light is captured at an end or a lateral surface of the optical fibers and the light is dissipated over the lateral surface or over the opposite end of the optical fibers.

6. The textile as claimed in claim 1, wherein the optical fibers are knitted, woven, tufted or sewn in the active outer surface or in the active inner surface.

7. A garment for a human comprising at least the textile as claimed in claim 1.

8. The garment as claimed in claim 7, wherein optical fibers cover at least partially the active outside surface, and the active outside surface is connected by the optical fibers with an active inside surface.

9. The garment as claimed in claim 8, wherein the active inside surface is in close contact to skin of the human, and the light captured by the active outside surface is transmitted by the optical fibers to the active inside surface whereupon the active inside surface dissipates the light to the human skin.

10. The garment as claimed in claim 7, wherein a spatial arrangement of the optical fibers covering the active outside surface and the active inside surface of the textile has a thermo-insulating effect.

11. The garment as claimed in claim 7 treats diseases occurring due to lack of light.

12. The garment as claimed in claim 7 which is outer clothing for men, women and children.

13. The garment as claimed in claim 12, adapted to illuminate the outer clothing with a light source transmitting light from the active inside surface to the active outside surface via the optical fibers.

14. A method of producing a garment comprising forming the textile according to claim 1 into a shape suitable to fit over and be worn by a human.

15. A textile having an active outside surface and an active inside surface comprising optical fibers covering at least partially the active outside surface, wherein the active outside surface captures light, which is transmitted by the optical fibers to the active inside surface, wherein the textile is made of a material that is at least one of stained, coated and impregnated with melanin or melanin derivatives, wherein the optical fibers are passed through a material layer of the textile, wherein light is captured with ends of the optical fibers on the active outside surface, whereupon the light is passed through the material layer of the textile by transmitting through the optical fibers to the active or optical inside surface, and wherein from opposing ends of the optical fibers which are arranged on the active inside surface or which form the active or optical inside surface the light is dissipated in a non-radiative way to the skin of a human who is covered with the textile and regulates a temperature of a microenvironment between the skin of the human and the textile.

16. A textile having an active outside surface and an active inside surface comprising optical fibers covering at least partially the active outside surface, wherein the active outside surface captures light, which is transmitted by the optical fibers to the active inside surface, wherein the textile provides light therapy treatment, wherein the optical fibers are passed through a material layer of the textile, wherein light is captured with ends of the optical fibers on the active outside surface, whereupon the light is passed through the material layer of the textile by transmitting through the optical fibers to the active or optical inside surface, and wherein from opposing ends of the optical fibers which are arranged on the active inside surface or which form the active or optical inside surface the light is dissipated in a non-radiative way to the skin of a human who is covered with the textile and regulates a temperature of a microenvironment between the skin of the human and the textile.

* * * * *